(12) United States Patent
Silverman et al.

(10) Patent No.: US 8,710,032 B2
(45) Date of Patent: Apr. 29, 2014

(54) **INHIBITORS OF THE MEVALONATE PATHWAY OF *STREPTOCOCCUS PNEUMONIAE***

(75) Inventors: Richard B. Silverman, Northbrook, IL (US); Takashi Kudoh, Kitaakita (JP)

(73) Assignee: Northwestern University, Evanston, IL (US)

( * ) Notice: Subject to any disclaimer, the term of this patent is extended or adjusted under 35 U.S.C. 154(b) by 1909 days.

(21) Appl. No.: 11/983,584

(22) Filed: Nov. 9, 2007

(65) Prior Publication Data
US 2011/0178043 A1    Jul. 21, 2011

Related U.S. Application Data

(60) Provisional application No. 60/858,081, filed on Nov. 9, 2006.

(51) Int. Cl.
| | |
|---|---|
| *A01N 57/00* | (2006.01) |
| *A61K 31/66* | (2006.01) |
| *A01N 37/00* | (2006.01) |
| *A61K 31/19* | (2006.01) |
| *A01N 37/10* | (2006.01) |
| *C07C 59/00* | (2006.01) |

(52) U.S. Cl.
USPC ............ 514/106; 514/557; 514/570; 562/579

(58) Field of Classification Search
None
See application file for complete search history.

(56) References Cited

PUBLICATIONS

Thibault et al. "Phase I study of lovastatin, an inhibitor of the mevalonate pathway, in patients with cancer.", Clin Cancer Res. Mar. 1996;2(3):483-91.*
Wilde et al. "Substrate and inhibitor specificity of mevalonate kinase determined with substrate analogues" Eur. J. Biochem. 221, 463-473 (1994).*
Klimov et al. (Biokhimiya (Moscow) (1971), 36(4), 851-6 CODEN: BIOHAO; ISSN: 0320-9725), English language abstract.*
Andreassi, II et al. Crystal structure of the *Streptococcus pneumoniae* mevalonate kinase in complex with diphosphomevalonate. Protein Sci., May 2007, vol. 16(5), pp. 983-989.
Andreassi, JL, II; Dabovic, K; Leyh, TS. *Streptococcus pneumoniae* Isoprenoid Biosynthesis Is Downregulated by Diphosphomevalonate: An Antimicrobial Target. Biochemistry 2004, 43, 16461-16466.
Bell, A; Davidson, AH; Earnshaw, C; Norrish, HK; Torr, RS; Trowbridge, DB; Warren, S. Synthesis of β-(Diphenylphosphinoyl) Ketones. J. Chem. Soc. Perkin Trans. 1:2879-91, (1983).
Bork, P; Sander, C; Valenci, A. Convergent evolution of similar enzymatic function on different protein folds: The hexokinase, ribokinase, and galactokinase families of sugar kinases. Protein Sci. 1993. 2:31-40.

Chênevert, R; Dasser, M. Chemoenzymatic Synthesis of the Microbial Elicitor (−)-Syringolide via a Fructose 1,6-Diphosphate Aldolase-Catalyzed Condensation Reaction. J. Org. Chem. 2000, 65, 4529-4531.
Corey, EJ; Schmidt, G. Useful Procedures for the Oxidation of Alcohols Involving Pyridinium Dichromate in Aprotic Media. Tetrahedron Lett. 1979. 20: 399-402.
Cornforth, JW; Cornforth, RH; Popják, G; Yengoyan, L. Studies on the Biosynthesis of Cholesterol. XX. Steric Course of Decarboxylation of 5-Pyrophosphomevalonate and of the Carbon to Carbon Bond Formation in the Biosynthesis of Farnesyl Pyrophosphate. J. Bio. Chem. 1966, 241:3970-87.
Inglis, TJJ; Rodrigues, F; Rigby, P; Norton, R; Currie, BJ. Comparison of the Susceptibilities of *Burkholderia pseudomallei* to Meropenem and Ceftazidime by Conventional and Intracellular Methods. Antimicrobial Agents and Chemotherapy, 2004. 48:2999-3005.
Iyengar, R; Cardemil, E; Frey, PA. Mevalonate-5-diphosphate Decarboxylase: Stereochemical Course of ATP-Dependent Phosphorylation of Mevalonate 5-Diphosphate. Biochemistry, 1986, 25:4693-8.
Ji, H; Li, H; Flinspach, M; Poulos, TL; Silverman, RB. Computer Modeling of Selective Regions in the Active Site of Nitric Oxide Synthases: Implication for the Design of Isoform-Selective Inhibitors. J. Med. Chem. 2003, 46, 5700-11.
Kazuta, Y; Matsuda, A; Shuto, S. Development of Versatile cis- and trans-Dicarbon-Substituted Chiral Cyclopropane Units: Synthesis of (1S,2R)- and (1R,2R)-2-Aminomethyl-1-(1H-imidazol-4-yl)cyclopropanes and Their Enantiomers as Conformationally Restricted Analogues of Histamine. J. Org. Chem. 2002, 167, 669-1677.
Knipe, AC; Stirling, CJM. Elimination-Addition. Part XV. Rates of Reactions of ω-Bromoalkyl p-Tolyl Sulphides with Alkoxides: the Role of Neighbouring Group Participation by Sulphur and the Involvement of Ion-pair Equilibria. J. Chem. Soc. (B), 1968, 1218-23.
Knipe, AC; Stirling, CJM. Elimination-Addition. Part XIII. Reactions of ω-Bromoalkyl p-Tolyl Sulphones with Bases: The Role of Inductive Effects in Elimination and Substitution. J. Chem. Soc. (B), 1967, 808-13.
Lesburg, CA; Zhai, G. Crystal Structure of Pentalenene Synthase: Mechanistic Insights on Terpenoid Cyclization Reactions in Biology. Science 1997, 277:1820-4.
Pilloff, D; Dabovic, K; Romanowski, MJ; Bonanno, JB; Doherty, M; Burley, SK; Leyh, TS. The Kinetic Mechanism of Phosphomevalonate Kinase. J. Biol. Chem. 2003, 278: 4510-4515.
Reardon, JE; Abeles, RH. Inhibition of Cholesterol Biosynthesis by Fluorinated Mevalonate Analogues. Biochemistry 1987, 26, 4717-4722.
Romanowski, MJ; Bonanno, JB; Burley, SK. Crystal Structure of the *Streptococcus pneumoniae* Phosphomevalonate Kinase, a Member of the GHMP Kinase Superfamily. Proteins: Structure, Function and Genetics 47:568-571 (2002).

(Continued)

*Primary Examiner* — James D Anderson
*Assistant Examiner* — William Lee
(74) *Attorney, Agent, or Firm* — Reinhart Boerner Van Deuren s.c.

(57) ABSTRACT

Compounds and related methods as can be used for selective mevalonate pathway inhibitors.

7 Claims, 5 Drawing Sheets

(56) References Cited

PUBLICATIONS

Silverman, RB; Olson, GT. Mechanism of Inactivation of γ-Aminobutyric Acid Aminotransferase by 3-Hydrazinopropionic Acid. J. Org. Chem. 1995, 60, 6232-6234.

Thoden, JB, Timson, DJ; Reece, RJ; Holden, HM. Molecular Structure of Human Galactokinase: Implications for Type II Galactosemia. J. Biol. Chem. 2005, 280: 9662-70.

Wilding, EL; Brown, JR; Bryant, AP; Chalker, AF; Holmes, DJ; Ingraham, KA; Iordanescu, S; So, CY; Rosenberg, M.; Gwynn, MN. Identification, Evolution, and Essentiality of the Mevalonate Pathway for Isopentenyl Diphosphate Biosynthesis in Gram-Positive Cocci. J. Bacteriol. 2000. 182: 4319-27.

Wong, K-T; Hung, Y-Y. A Convenient One-Pot Synthesis of Homoallylic Halides and 1,3-Butadienes. Tetrahedron Lett. 44 (2003) 8033-8036.

Yamashita, A; Toy, A; Scahill, TA. Synthesis of Khellin and Its Analogues Via Chromium Carbene Complexes. J. Org. Chem. 1989, 54, 3625-3634.

Yang, D; Shipman, LW; Roessner, CA; Scott, AL; Sacchettini, JC. Structure of the *Methanococcus jannaschii* Mevalonate Kinase, a Member of the GHMP Kinase Superfamily. J. Biol. Chem. 2002, 277: 9462-7.

Yasuda, M; Yamashita, T; Matsumoto, T; Shima. K. Enantioselective Total Synthesis of (+)-Pumiliotoxin A. J. Org. Chem. 1985, 50, 3669-3670.

* cited by examiner

Fig. 3 a, R = CH$_2$F
b, R = CHF$_2$
c, R = CF$_3$

R=alkyl (2 - about 6 carbons), substituted alkyl (2 - about 6 carbons), aryl, substituted aryl, heteroaryl and substituted heteroaryl

Fig. 6

| Sample | Structure | Sample | Structure |
|---|---|---|---|
| TK1 | 4-hydroxy-4-vinyl-tetrahydro-2H-pyran-2-one | TK7 | 4-hydroxy-4-(prop-1-en-2-yl)-tetrahydro-2H-pyran-2-one |
| TK2 | 4-ethyl-4-hydroxy-tetrahydro-2H-pyran-2-one | TK8 | 4-hydroxy-4-isopropyl-tetrahydro-2H-pyran-2-one |
| TK3 | 4-hydroxy-4-propyl-tetrahydro-2H-pyran-2-one | TK9 | 4-allyl-4-hydroxy-tetrahydro-2H-pyran-2-one |
| TK4 | 4-butyl-4-hydroxy-tetrahydro-2H-pyran-2-one | TK10 | 4-ethynyl-4-hydroxy-tetrahydro-2H-pyran-2-one |
| TK5 | 4-hydroxy-4-isobutyl-tetrahydro-2H-pyran-2-one | TK11 | 4-hydroxy-4-(prop-1-ynyl)-tetrahydro-2H-pyran-2-one |
| TK6 | 4-(cyclopropylmethyl)-4-hydroxy-tetrahydro-2H-pyran-2-one | | |

Fig. 7

| Results with Mevalonate Analogues | | |
|---|---|---|
| Compound | MK substrate [a](V/Vc) | PMK substrate |
| 1 | 1.2 | Yes |
| 2 | 0.11 | Yes |
| 3 | 0.16 | No |
| 4 | 0.040 | No |
| 5 | 0.021 | No |
| 6 | 0.215 | Yes |
| 7 | 0.13 | No |
| 8 | - | No |
| 9 | 0.342 | No |
| 10 | 1.1 | Yes |
| 11 | .052 | No |
| [a]V/Vc velocity with analogue relative to mevalonate | | |

Fig. 8

INHIBITORS OF THE MEVALONATE PATHWAY OF *STREPTOCOCCUS PNEUMONIAE*

This application claims priority benefit from provisional application Ser. No. 60/858,081 filed on Nov. 9, 2006, the entirety of which is incorporated herein by reference.

This invention was made with government support under Grant No. AI068989 awarded by the National Institutes of Health. The government has certain rights in the invention.

BACKGROUND OF THE INVENTION

*Streptococcus pneumoniae* exacts an enormous toll on humanity. This pernicious organism kills approximately 3700 people per day, the majority of whom are children below the age of five. The populations at greatest risk for suffering life-threatening infections are the elderly and the young, immunosuppressed and diabetic individuals, and those with hematologic malignancies and renal failure. In the United States, on a per annum basis, the organism is estimated to cause 3000 cases of meningitis, 50,000 cases of bacterimia, 500,000 cases of *pneumoniae*, and 7 million episodes of acute otitis media (inner ear infection) that result in one million doctor visits and 5 billion dollars in related expenses.

Mankind has long suffered the debilitating consequences of *S. pneumoniae* infection. The organism was first isolated by Louis Pasteur in 1881 and was identified as a primary cause of lobular pneumonia soon thereafter. There are now more than 90 distinct serotypes (46 serogroups), each with a different propensity to cause human disease. Our previous battles with this organism have taught us that our current strategies (vaccines and antibiotics) provide temporary solutions, rather than endpoints, for the problem. During the last century, multiple antibiotic classes were brought forward against the organism which responds, seemingly inevitably, using a combination of spontaneous mutagenesis, DNA transfer among related organisms, and amplification by positive selection, to circumvent the metabolic blockages set in place by the antibiotics. Once an antibiotic-resistant strain emerges, it spreads quickly via colonization-pneumococci are found in the nasopharynx of 15% of well adults and up to 65% of children in child-care settings. It is generally agreed that successful containment of this organism requires constant vigilance (large-scale antibiotic-resistance surveillance efforts are underway at the Centers for Disease Control), the stringent use of antibiotics, and a pipeline of drugs and vaccines that enable us to respond quickly to changes in the streptococcal population. Unfortunately, the development of new antibiotics is no longer considered economically feasible by the pharmaceutical industry. Hence, our pipelines are drying up even as strains resistant to our last-line antibiotics are beginning to appear. The current pharmaco-economic landscape suggests that the financial burden for future antibiotic development will fall primarily on the shoulders of governmental funding agencies in economically advantaged countries. The threat of domestic and foreign strains of multiple-drug-resistant *S. pneumoniae* continues to mount, and is extremely serious.

There is however, a molecular Achille's heal in *S. pneumoniae*: mevalonate kinase, the first enzyme in the mevalonate pathway harbors an allosteric site that can be used to switch-off isoprenoid biosynthesis, which is essential for growth of the organism. (Andreassi J L, 2nd, Dabovic K, Leyh T S. 2004. *Streptococcus pneumoniae* isoprenoid biosynthesis is downregulated by diphosphomevalonate: an antimicrobial target. *Biochemistry* 43: 16461-6) Diphosphomevalonate (DPM), an intermediate in the pathway, binds to the allosteric site with high affinity ($K_i$=400 nM) and reversibly inhibits the enzyme. *S. pneumoniae* mutants in which the mevalonate pathway has been inactivated are unable to survive in the mouse lung, and the levels of mevalonate in serum appear insufficient to support their growth. These important biological studies validate the mevalonate pathway as a target for antimicrobial research. Such studies also demonstrated that the human mevalonate kinase isozyme is not affected by the allostere (DPM)—it does not have a functioning allosteric site. The implication of these findings is that it may be possible to inhibit *S. pneumoniae*, and other low-G+C gram-positive streptococcal pathogens, with little influence on human metabolism.

The Mevalonate Pathway.

Figure 1:
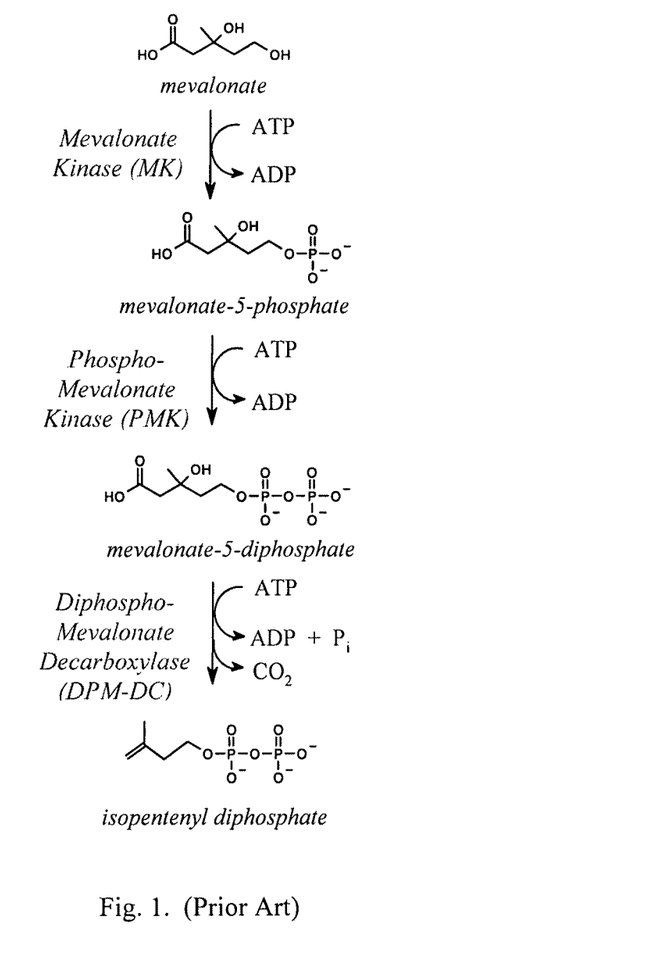
FIG. 1. The Mevalonate Pathway.

The pathway is comprised of three consecutive reactions (see FIG. 1) that are catalyzed by the enzymes mevalonate kinase (MK), phosphomevalonate kinase (PMK) and diphospho-mevalonate kinase decarboxylase (DPM-DC). The end-product of the pathway, isopentenyl diphosphate, is the 5-carbon building block used for the biosynthesis of isoprenoids, a diverse family of roughly 23,000 biologically active small molecules that includes cholesterol, steroid hormones, bile acids, electron transport carriers, carotenoids, vitamin A, Taxol, farnesyl diphosphate, and numerous other interesting compound classes. Given the ubiquity and metabolic significance of isoprenoids, it is not surprising that the mevalonate pathway is considered essential for the survival of organisms that require it for isoprenoid biosynthesis.

The GHMP Kinase Family.

MK, PMK and DPM-DC are each members of the GHMP-kinase superfamily. Continued study will provide mechanistic and structural comparisons across the superfamily that will enhance understanding of the catalytic machinery shared by all members of the family and the changes that enable both γ-phosphoryl transfer to different acceptors and addition of the decarboxylation chemistry. The superfamily began taking shape in 1988 when the three conserved sequence-motifs (I-III) used to recognize family members was first reported. Soon thereafter, the motifs were associated with the structural elements that carry out functions common to the family—ATP binding and γ-phosphoryl transfer. In 1993 the four "sugar kinases" from which the GHMP acronym derives (Galactokinase, Homoserine kinase, Mevalonate kinase and Phosphomevalonate kinase) were gathered together, forming the family. Currently, the Protein Families Database (Pfam) associates 841 unique protein sequences with the superfamily, approximately one-tenth of which do not yet have a defined function. The superfamily has evolved to produce nominally seven different catalysts (mevalonate kinase, phosphomevalonate kinase, diphosphomevalonate decarboxylase, archeal shikimate kinase, galactokinase, homoserine kinase, and 4-(cytidine 5'-diphospho)-2c-methyl-d-erythritol kinase) each designed to transfer the γ-phosphoryl group of ATP to a different acceptor, and a putative transcription factor, Xol-1, that regulates development in *C. elegans*. Of the seven enzymes, six kinases and one decarboxylase, two have been linked to inherited human disease, two are involved in the biosynthesis of aromatic and non-aromatic amino acids, folates and ubiquinones, one is needed to deliver galactose to the glycolytic pathway, and four participate in either the mevalonate or non-mevalonate dependent synthesis of isoprenoids.

The relevance to human disease extends beyond the borders of antibiotic development. Mevalonic aciduria (MVA) and hyperimmunoglobulinemia D (HIDS), both orphan diseases, are caused by allelic changes in motif III of MK. HIDS, characterized by febrile attacks, abdominal pain, arthralgia and rashes, does not significantly reduce life expectancy, while the symptoms of MVA range from mild neurological disorder to progressive fatal disease and neonatal death. The MK A334T mutation found in MVA patients causes a 50-fold decrease in $V_{max}$, resulting in a life-threatening increase in levels of mevalonate in plasma. The analogous mutation in the S. pneumoniae PMK causes similar effects, $k_{cat}$ decreases 63-fold. These two enzymes catalyze different reactions (transfer to a primary hydroxyl or phosphate monoester); yet, the catalytic consequences of homologous mutations in conserved regions of the superfamily are similar. Thus, the lessons gleaned from one family member do, in certain cases, extrapolate well to others. Galactokinase (GK) deficiency results in excess galactose and galactitol which causes cell-death in the lens epithelium, producing cataracts. Position 334 mutations in GK cause cataracts in humans, and the catalytic consequences of these mutations have not be determined. Position 334 is located in Motif I, it is chemically is well conserved, and structures of GK (P. furiosus) and PMK support that it performs similar catalytic functions across the family. Mutations in PMK at this position cause pronounced effects on the steady-state affinity of the non-nucleotide substrate, variable effects (tightening to weakening) on the nucleotide affinity, and small effects on $k_{cat}$. These findings led to the prediction that the metabolic lesion resulting from the cataract-causing GK mutations is a decrease in the steady-state affinity of the enzyme for galactose. These examples demonstrate how catalytic paradigms, established using a representative member of a protein family, can provide testable hypotheses regarding the molecular etiology of disease.

The Protein Database (PDB) contains the structures of seven different members of the family. Sequence identity among the seven is low (10-20%) yet they share a great deal of three-dimensional similarity, the $C_\alpha$ RMSDs range from 2.6-4.0 Å. The structural scaffold has been well maintained over evolutionary time (particularly the ATP-binding and γ-phosphoryl transfer elements) while residues in the γ-phosphoryl acceptor pocket have been allowed to drift, sculpting active sites with altered specificity and, in the case of DPM-DC, additional chemistry.

SUMMARY OF THE INVENTION

In light of the foregoing, it is an object of the present invention to provide various compounds, compositions and/or methods for their use in the study and/or treatment of Streptococcus pneumoniae. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

As can relate to certain other embodiments, it can be an object of this invention to provide selective inhibitors of mevalonate kinase or other enzymes in the cholesterol biosynthetic pathway of S. pneumoniae, such inhibitors including but not limited to compounds of the sort described herein.

As can relate to certain other embodiments, it can be another object of the present invention to provide such inhibitory compounds, related compositions and/or methods of use in the treatment of infectious S. pneumoniae.

Other objects, feature, benefits and advantages of this invention will be apparent from this summary and the following descriptions of certain embodiments, and will be readily apparent to those skilled in the art having knowledge of various enzymatic pathways and mechanistic considerations, together with the design and synthesis of corresponding inhibitors. Such objects, features, benefits and advantages will be apparent from above as taken into conjunction with the accompanying examples, data, figures and all reasonable inferences to be drawn therefrom, alone or with consideration of the references incorporated herein.

In part, the present invention can be directed to a mevalonate pathway inhibitor compound of a formula wherein $R_1$ can be selected from $C_2$ to about $C_6$ alkyl and including linear, branched and cycloalkyl (e.g., cyclopropyl), $C_2$ to about $C_6$ substituted alkyl, $C_2$ to about $C_6$ alkenyl, $C_2$ to about $C_6$ substituted alkenyl, $C_2$ to about $C_6$ alkynyl, $C_2$ to about $C_6$ substituted alkynyl, aryl, substituted aryl, heteroaryl and substituted heteroaryl moieties; and $R_2$ and $R_{2'}$ are independently selected from H, monophosphate and diphosphate moieties. Such compounds can be present as their salts, esters, hydrates and solvates thereof.

In certain embodiments of such an inhibitor compound, $R_1$ can be selected from $C_2$ to $C_4$ alkyl moieties. In certain such embodiments, $R_1$ can be selected from cyclopropyl and methylenecyclopropyl moieties. In certain other embodiments, $R_1$ can be selected from vinyl and acetylenyl moieties. Regardless of choice of $R_1$, $R_2$ and $R_{2'}$ can be H. In certain such embodiments, where $R_{2'}$ is H, such an inhibitor compound can comprise the intramolecular cyclization thereof. As illustrated below, such a compound can be used to contact, interact with, bind to and/or inhibit an enzyme in a mevalonate biosynthetic pathway.

In part, the present invention can also be directed to a mevalonate pathway inhibitor compound of a formula wherein $R_1$ can be selected from $C_2$ to about $C_6$ alkyl and including linear, branched and cycloalkyl (e.g., cyclopropyl), $C_2$ to about $C_6$ substituted alkyl, $C_2$ to about $C_6$ alkenyl, $C_2$ to about $C_6$ substituted alkenyl, $C_2$ to about $C_6$ alkynyl, $C_2$ to about $C_6$ substituted alkynyl, aryl, substituted aryl, heteroaryl and substituted heteroaryl moieties; and salts, esters, hydrates and solvates thereof.

In certain embodiments, $R_1$ can be as described above. Regardless, such a compound can interact with an enzyme of a mevalonate biosynthetic pathway, and such a compound can be complexed with, bound to or otherwise associated with such an enzyme. In certain such embodiments, the enzyme can be selected from a mevalonate kinase, a diphosphomevalonate decarboxylase and combinations thereof. Without limitation, such an enzyme can be of Streptococcus pneumoniae.

Accordingly, in part, the present invention can also be directed to a method of treating Streptococcus pneumoniae. Such a method can comprise contacting Streptococcus pneumoniae with an effective amount of a compound of formula wherein $R_1$ can be selected from moieties of the sort described above. In certain such embodiments, such a compound and/or combinations thereof can be present in an amount at least partially sufficient to bind or otherwise interact with an enzyme of the mevalonate pathway of such an organism, inhibit the pathway and/or inactivate the organism.

In part, the present invention can also be directed to a method of using the C-3 substituent of a mevalonate analog compound to affect an enzyme in a mevalonate biosynthetic pathway. Such a method can comprise contacting a mevalonate pathway enzyme with an effect amount of a compound of a formula wherein $R_1$, $R_2$ and $R_{2'}$ can be selected as described above and illustrated elsewhere herein. In certain embodiments, such a compound can be the hydrolysis product of a compound and of a formula wherein such a compound can be phosphorylated, as illustrated below. Regardless, in certain embodiments, such an enzyme can be selected from a mevalonate kinase, a diphosphomevalonate decarboxylase and combinations thereof. In certain such embodiments, such an enzyme can be bacterial, as can be derived from *Streptococcus pneumoniae* or present in the mevalonate pathyway thereof.

DETAILED DESCRIPTION OF THE DRAWINGS

DETAILED DESCRIPTION OF CERTAIN EMBODIMENTS

One or more of the following findings and considerations can relate to and support one or more non-limiting embodiments of the compounds, compositions and/or methods of this invention, together with the utility thereof, such findings and considerations as would be understood by those skilled in the art made aware of this invention.

DPM Regulation of Isoprenoid Biosynthesis in *S. Pneumoniae*.

Regulation of the isoprenoid biosynthetic pathway in *S. pneumoniae* was discovered during an attempt to enzymatically synthesize DPM from ATP and mevalonate using MK and PMK. Individually, either enzyme is capable of quantitative conversion of substrate to product. However, when the enzymes are added simultaneously, the forward reaction decelerates rapidly and little product is formed. Subsequently, DPM was shown to bind tightly to MK, $K_i$=500 nM, and to reduce turnover to less than 0.5%. An initial-rate study of the inhibition mechanism revealed that DPM binds noncompetitively vs both mevalonate and DPM. Thus, this nearly pure noncompetitive inhibitor binds at a site that is physically distinct from the substrate binding sites—an allosteric site. The allosteric nature of the site was confirmed in equilibrium binding studies that showed that the affinity of DPM for the apo (E) and ternary (E.AMPPNP.mev) forms of the enzyme were virtually identical, 630 and 530 nM respectively. The binding studies further revealed that DPM binds with a stoichiometry of 0.5 DPM/active site; the enzyme is a dimer. The stoichiometry was confirmed by NMR titration. To test the specificity of the allosteric site, the four structurally related isoprenoid metabolites that lie immediately downstream of DPM were tested as MK inhibitors—none showed significant inhibition. Down-regulation of this pathway is quite specific for DPM.

Figure 3:
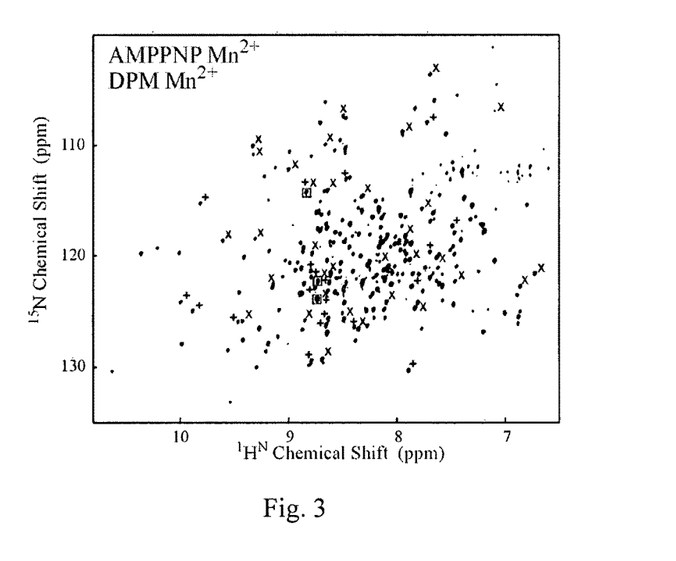
FIG. 3. Relaxation effects of $Mn^{2+}$ substitution on AMP-PNP and DPM complexes of MK mapped onto 900 MHz spectrum of the ternary-DPM complex. The labeled cross peaks disappear when $Mn^{2+}$ is substitute for $Mg^{2+}$ in MK AMPPNP $M^{2+}$ (+) or MK-DPM-$M^{2+}$ (x). Experimental conditions: MK (400 µM); or, MK (400 µM), $Mn^{2+}$ or $Mg^{2+}$ (200 µM) and DPM (450 µM); or, MK (400 µM), $Mn^{2+}$ or $Mg^{2+}$ (400 µM) and AMPPNP (10 mM)-Hepes/K$^+$ (25 mM, pH 8.0) KCl 50 mM), DTT (1.5 mM), T=25° C.

The findings that mevalonate-pathway *S. pneumoniae* mutants cannot survive in mouse lung or serum validated this pathway as an antibiotic target in animal models. Acting on the hypothesis that the primary sequence differences of the mammalian and streptococcal MKs might produce different DPM-inhibition characteristics, the human enzyme was cloned, expressed, purified and tested for DPM inhibition. The effect of DPM on the initial rate of the human and streptococcal enzymes was assessed using samples with matched catalytic poise ([substrates]~$K_m$, equivalent $V_m$). The results, compared in FIG. 3, demonstrate that the human enzyme is virtually unaffected at DPM concentrations that essentially completely inhibit the streptococcal system. The highly isozyme-specific nature of the DPM inhibition highly recommends the allosteric site as a target, and holds the promise of anti-streptococcal antibiotics that do not influence human metabolism.

First Generation Drug.

Several compounds were designed to inhibit DPM-DC and control cholesterol biosynthesis. In one such compound, each of the $C_6$-methyl protons of mevalonate are replaced with fluorine (6,6,6-trifluoromevalonate, $F_3$-mev). Given DPM inhibition of MK, and excellent inhibition of rat liver DPM-DC by $F_3$-DPM ($K_i$=0.5 µM) it was hoped that $F_3$-DPM might inhibit both MK and DPM-DC from *S. pneumoniae*, and, if so, be used as a bacteriostatic or bacteriocidal agent. To test this hypothesis, $F_3$-mev was converted enzymatically to $F_3$-DPM, which was shown to be an excellent inhibitor of both MK ($K_i$=570 nM) and DPM-DC ($K_i$=50 nM) from *S. pneumoniae*. Encouraged, $F_3$-DPM was tested as an antibiotic against *S. pneumoniae*. To avoid the possible obstacles of phosphatase degradation of DPM and transporting a highly charged anion across the cell wall, a prodrug strategy that relies on conversion of $F_3$-mev to $F_3$-DPM in the cytosol was used. $F_3$-mev conversion to $F_3$-DPM and consequent inhibition of DPM-DC occurs in rat liver extracts. The linear and lactone forms of statins, which target an early step in the isoprenoid pathway, show widely different potencies; consequently, both forms of $F_3$-mev were tested as inhibitors. Serial dilutions of $F_3$-mev were added to Meuller-Hinton Broth, a horse-blood based medium, containing ~7.5×10⁷ cells of either an infectious (ATCC 49619) or non-infectious (R6) strain of *S. pneumoniae*. The cultures containing $F_3$-mev were incubated for 24 hours at 35° C. and plated to assess viability. The linear form of $F_3$-mev had little effect; confluent growth was observed on all plates; in contrast, the lactone is clearly a bacteriocide—less than 0.0001% of either strain survived at 100-200 µg/ml of the lactone. In rat liver extracts, the monofluoro derivative was 50-times more effective in inhibiting incorporation of mevalonate into nonsaponifiable lipids than $F_3$-mev, and it is a 50-fold better inhibitor of DPM-DC. A similar effect on antibiotic potency against *S. pneumoniae* would lower the >99% kill level to 2-4 µg/ml.

Structure of the MK.DPM complex.

1560 crystallization conditions (four enzyme ligand combinations, 390 conditions/combination) were tested to obtain diffraction quality crystals for x-ray determination of the DPM-binding site structure. Crystals belonging to space group P3$_1$21 were prepared by the sitting drop under oil method from solutions containing 200 µM MK active sites, 20% (v/v) polyethylene glycol 400, 100 mM sodium formate, 5.0 mM AMPPNP, 0.25 mM DPM and 6 mM Mg$^{2+}$ at ambient temperature. Two x-ray diffraction data sets were measured with a Rigaku R-Axis IV$^{++}$ detector and RU-H3R rotating anode X-ray generator. A 2.8 Å data set from a crystal derivatized with trimethyllead acetate provided the initial phase angle determination. A preliminary atomic model derived from this analysis was used to solve a higher resolution native data set. The final atomic model of MK in complex with DPM and Mg$^{2+}$ contained one subunit of the dimeric enzyme per asymmetric unit and was refined to an R-factor of 21.1% (R-free=27.0%) at 2.5 Å. Although APMPNP was included in the crystallization solutions, no evidence of its presence was found in the crystal structure.

The overall structure of the MK.DPM complex resembles that of other GHMP kinases. X-Ray structures of two MK isozymes have been determined (E.ATP complex (rat) and apo enzyme (*M. jannaschii*. Neither isozyme exhibits strong sequence similarity with *S. pneumoniae* MK (rat: 23% identity, 38% similarity, and considerably longer (396 vs 292 residues); *jannaschii*: 25% identity, 45% similarity, comparable size (312 vs 292 residues), and certain isozymes (e.g., human MK) are insensitive to DPM. It should prove valuable to correlate sequence and inhibition patterns of isozymes in regions that encode the allosteric binding-site. Such a correlation is expected to provide the sequence hallmarks of DPM-sensitivity and thereby help to define the spectrum of organisms against which a DPM-based drug might be effective. Furthermore, it will classify organisms according to their isoprenoid metabolism.

The E.DPM.Mg$^{2+}$ structure presents one molecule of DPM at each subunit, a stoichiometry that is in conflict with that obtained from equilibrium-binding measurements, 1 DPM/dimer. The two molecules of DPM are symmetrically disposed about a central pore, as discussed below. The DPM-binding pocket in the structure is, in-fact, the active-site of the enzyme, and comparison with other GHMP kinase structures reveals that it is positioned precisely as expected for a substrate. Hence, DPM is predicted to act as a competitive inhibitor vs mevalonate, which is not observed, and positioning of the DPM pyrophosphoryl moiety suggest that it might also be competitive vs ATP.

The predictions of the E.DPM.Mg$^{2+}$ structure stand at odds with the results of equilibrium and initial-rate studies regarding both the DPM-binding stoichiometry and the uniqueness of the DPM-binding site. It is not surprising that DPM, whose structure encompasses mevalonate and an ATP fragment, can bind at the MK active-site. Attempts to drive DPM from the active site and into the allosteric site using high [ATP]/[DPM] and [mevalonate]/[DPM] ratios were unsuccessful—crystals of the E.DPM.Mg$^{2+}$ complex were obtained. Conditions designed to crystallize binary and ternary substrate complexes of MK did not yield crystals. Thus far, the enzyme appears solely able to trap DPM at it active site. Closer inspection of the structure reveals atypical features. Five P-loop residues are disordered, this is not seen in other GHMP kinase structures, and the helix and loop that form the base-interaction section of the binding pocket is not fully structured—the loop that interacts with the base has not been "lifted" into its interaction position because the helix on which it "stands" is foreshortened to ~half of the length seen in other structures. It is as if the structure represents a snapshot of the protein assembling its active site.

Acting on the hypothesis that DPM is not positioned at the allosteric site in the E.DPM.Mg$^{2+}$ structure, the structure was studied for additional plausible binding sites. The 1 DPM/dimer stoichiometry suggests that DPM might bind at a single, unique, symmetrically positioned monomer interface. Remarkably, surrounding the central axis of the molecule is a small pore (~5 Å diameter) that opens into a cavity in the core of the molecule whose dimensions and chemical disposition seem a near perfect fit for DPM. Several amino acid side chains were removed from one subunit to provide clear visual access into the cavity. Except for its protruding carboxyl tail, DPM would otherwise appear completely engulfed by the cavity. The positively charged, back-wall of the cavity shows excellent shape and chemical complementarity to the pyrophosphoryl-group of DPM, and the complementarity continues as the cavity turns largely hydrophobic in the sections that would interact with the aliphatic regions of DPM. This cavity is the most likely candidate for the allosteric DPM-binding pocket, as can be confirmed by determining the structure of the DPM.MK complex using X-ray diffraction and/or high resolution NMR.

Phosphomevalonate Kinase.

PMK is the only member of the GHMP kinase family designed to transfer a phosphoryl group between two phosphate monoesters, rather than a monoester and hydroxyl moiety. Structural comparisons of PMK with other family members will offer intriguing examples of natural catalytic adaptation. The enzyme, a 37 kDa monomer, is robust and well behaved: it is soluble to >1 mM active sites without solubilizing agents, it expresses well in *E. coli* (~15 mg pure enzyme/liter rich media), and can be stored for >6 months at −80° C. without loss of activity. Catalysis occurs via a random bi-bi mechanism, and the initial-rate kinetic constants for the forward and reverse reactions were determined. The equilibrium constant slightly favors DPM formation ($K_{eq}$=1.7, pH 8.0, T=30° C.). The slow turnover of the enzyme ($k_{cat\ (forward)}$= 4.3 s$^{-1}$, $k_{cat\ (reverse)}$=3.9 s$^{-1}$) recommends it well for the pre-steady state quenched—and stopped-flow studies—such studies have not been performed on any of the members of the GHMP kinase family.

PMK was used as a model GHMP kinase to define the molecular functions of conserved, surface-resides of the GHMP kinase family. Surface resides are the primary interface with which and enzymes interact with its environment. A profile of the functions of these residues should extrapolate well across the family. Sequence and structural conservation criteria were used to define the candidate residues. The 142 well-defined sequences in the family were grouped according to EC number and compared within and across groups to assess conservation. Surface accessibility was then assessed by mapping the conserved residues onto the PMK structure. Structurally conserved surface residues screened out by sequence conservation criteria were identified by comparison of family structures. Ultimately, nine resides, five of which fall in the conserved motifs, were selected for further study. Each residue was substituted, via mutagenesis, for ala and/or a chemically similar residue, and the effects of substitution on the initial-rate parameters of the DPM-forming reaction were determined. These studies offer predictions regarding the molecular etiology of an inherited galactosemia that results in cataract formation, and provide an excellent foundation for further, more in-depth, mechanistic study.

The Ternary PMK Complex (PMK.AMPPNP.Pmev).

The *S. pneumoniae* Apo-PMK structure has been solved. To gain further insight into the molecular basis of catalysis in this system, and to contribute to an understanding of how structural differences across the family dictate substrate and mechanistic specificity, the ternary complex of PMK, from *S. pneumoniae*, was crystallized to solve its structure. The complex crystallizes readily. Many of the 390 crystallization conditions yielded crystals. Crystals belonging to space group P2$_1$2$_1$2 were prepared by the sitting drop under oil method from solutions containing 160 μM PMK active sites, 11% (w/v) polyethylene glycol, 12.5 mM Hepes, 25 mM MES, 50 mM KCl, 0.75 mM DTT, 0.5 mM Pmev, 5.0 mM AMPPNP and 6.0 mM MgCl$_2$ at ambient temperature. A single x-ray diffraction data set was measured to 1.9 Å. The structure was solved by molecular replacement and refined to an R-factor of 18.5% (R-free=20.8%) and contains a single molecule of monomeric MK in complex with AMPPNP, Pmev and Mg$^{2+}$.

Among the mechanistic lessons gleaned from the structure is the remarkable way in which PMK seems to use the essential divalent cation, Mg$^{2+}$, to accomplish catalysis. Binary and ternary complex structures of other GHMP kinases show Mg$^{2+}$ either in β,γ- or α,β,γ-coordination with ATP, and the E.ATP complex of PMK will likely exhibit similar coordination. However, the PMK ternary complex shows Mg$^{2+}$ straddling the donor and recipient phosphoryl groups where it is perfectly positioned to contribute to both ground- and transition-state stabilization of the transfer reaction. It seems that Pmev binding encourages Mg$^{2+}$ to migrate from its coordination in the E.ATP complex into a catalytically active, bridging position in the substrate ternary complex. It is reasonable, and was shown in the MK.DPM complex, that Mg$^{2+}$ will be coordinated to the pyrophosphoryl-moiety of DPM in the product central complex. If so, the cation will have been "handed" from the nucleotide to DPM during the transfer reaction. Consider that such state-dependent positioning allows Mg$^{2+}$ to differentially stabilize complexes on each side of the transfer, thereby "tuning" catalysis.

Another observation is that the active site contains a significant quantity of water. Nine water molecules are found either bound to, or in the near vicinity, of the phosphoryl-groups of AMPPNP and Pmev. Thus, PMK is challenged to position reactive groups to prevent reaction with water lying in close proximity. The water forms what are likely to be quasi-static structures that contribute to the stability and reactivity at the active site.

A third and final example of how PMK accomplishes catalysis presents one of several considerable structural changes that the system undergoes in moving from the apo to the ternary complex. At the end of the refolding the substrates are essentially completely encased in a shell of protein. The figure focuses on how the P-loop reorganizes to prepare for catalysis. The P-loop regions of the apo and ternary structures are compared. Only the pyrophosphoryl-group of ATP is shown; the β-phosphorous is labeled. In the apo complex, K101 is hydrogen bonded to the carboxylate of E98, situated at the tip of a helical element, and K100 is not tethered to the protein. Upon binding of substrates, the E98 hydrogen bond is broken as K101 swings 180° toward substrate, passing K100 which seems to move in the opposite direction, unraveling the helical element, to establish a hydrogen bond with the carbonyl oxygen of K208. This "catalytic switch" delivers K101 into position to electrostatically stabilize the development of negative charge that occurs at the β,γ-bridging position during the transition state—a remarkable example of how order creates function.

Structure and Function by NMR. Despite its utility, the crystal structure of the MK.DPM complex predicts DPM-binding properties that stand at odds with the non-crystallographic data on two important points. First, the structure shows a DPM/active-site stoichiometry of 1:1, whereas DPM-binding data indicate that the DPM/allosteric-site stoichiometry is 1:2. Second, the region of the active-site occupied by DPM in the structure suggests that its binding should be competitive vs both ATP and mevalonate—this is not observed in initial-rate or equilibrium-binding experiments (DPM binding is noncompetitive vs either substrate). As long as these inconsistencies stand, it is imprudent to use the crystallographically determined DPM-binding pocket as a structural model for inhibitor design. To reconcile these discrepancies, an alternative structural technique, NMR, was used to test the hypothesis that the DPM-binding site seen in the crystal structure is not, in fact, the alloseric binding-site. Uniformly enriched $^{15}$N-labelled mevalonate kinase was expressed in *E. coli*, purified, concentrated to 400 μM, and a TROSY spectrum that detects through-bond $^{15}$N-$^{1}$H interactions was obtained at 600 MHz. This exercise revealed that MK is well suited to NMR investigation. The protein is stable during data acquisition for >7 days, and the spectral peaks are well resolved (192 of the 282 cross-peaks were identified with very good signal-to-noise after 12 minutes of data acquisition).

Figure 2:
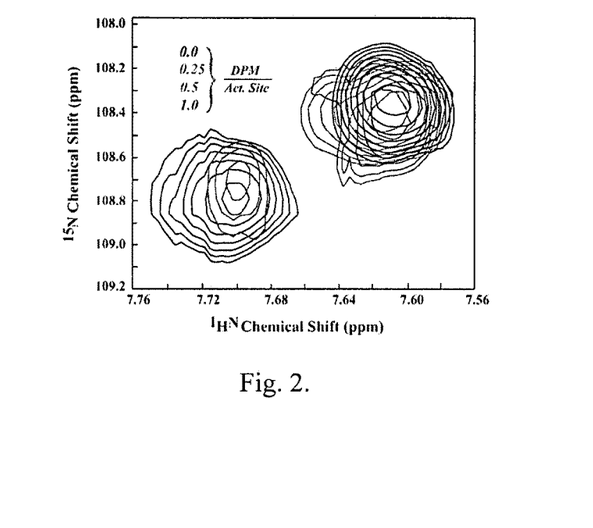
FIG. 2. DPM/MK Stoichiometry by $^{15}N$-$^1H$ TROSY NMR. DPM binding shifts the APO cross peak (black) from position A to B. Addition of DPM to 100 µM (0.25 active-site equivalents) shifts~half of the APO signal to B. 0.50 equivalents shifts the entire signal, further addition (blue) has no effect. Conditions: Hepes/K$^+$ (25 mM, pH 7.0), KCl (50 mM), DTT (1.5 mM), T=25° C.

To determine whether, under conditions of the NMR experiment, the DPM-binding stoichiometry is consistent with the crystallographic (1 per active site) or ligand-binding (0.5 per active site) data, a DPM titration of the binding-induced chemical shift of the protein was performed. The effects of increasing [DPM] on a representative peak in the TROSY spectrum is shown in FIG. 2. The MK active-site concentration (400 μM) is ~800×$K_{d\ DPM}$ (0.5 μM); hence, DPM will bind essentially stoichiometrically until it is in excess of its binding site. The titration shows the chemical shift of a representative cross-peak as a function of [DPM] at 0, 0.25, 0.50 and 1.0 active-site equivalents of DPM. The resonance occurs at position A in the absence of DPM, and is shifted to B by the binding of DPM. The addition of 0.25 equivalents of DPM is sufficient to shift roughly half of the signal to B; at 0.50 equivalents all of the intensity has shifted, and further addition of DPM has no effect. Virtually all of the other shifted resonances in the spectrum exhibited similar saturation patterns. Thus, under the conditions of the NMR experiment, the stoichiometry is 1:2. This ratio agrees with the DPM-binding and inhibition data, and strongly supports that the NMR structure of the MK.DPM complex will reveal how DPM binds at the allosteric site and provide the structural target against which novel, *streptococcus*-specific antibiotics can be developed.

$^{15}$N-$^1$H TROSY spectra (600 MHz) of the apo, ternary (E.AMPPNP.Mev) and ternary.DPM complexes of MK exhibit comparable resolution, and are distinct from one another. Underlying the unique features of these spectra are the structural differences that define how MK responds to and interacts with its ligands, positions and prepares its substrates for catalysis, and how DPM-binding allosterically disrupts that positioning. These behaviors, clearly accessible by NMR, can be studied to establish a structural and functional paradigm for the catalytic and allosteric properties of the GHMP kinase family. DPM binding to the apo and ternary MK-complexes causes ~25 backbone-amide resonances to undergo essentially identical chemical shift changes, which suggests that DPM and substrates bind at separate sites. Furthermore, DPM binding does not split peaks in the spectrum; thus, the backbone changes that cause the shifts are identical in both subunits. Satisfying the constraints of identical interactions with both subunits and a binding stoichiometry of 0.5/subunit requires DPM to bind at a 2-fold symmetric interface between the subunits. The central pore satisfies both criteria.

The tri- and di-polyphosphate chains of AMPPNP and DPM provide the opportunity to insert a paramagnetic probe, $Mn^{2+}$, directly into the active- and allosteric-sites of MK. The unpaired electron spin of $Mn^{2+}$ (S=5/2) efficiently relaxes nearby nuclear spins, and the enhanced $T_2$ relaxation causes their resonances to broaden in a distance ($1/r_6$) dependent fashion. Signals from nuclei within an ~10 Å radius of $Mn^{2+}$ are broadened essentially into the baseline whereas those in the 10-25 Å shell are less severely attenuated. TROSY spectra of the E.$Mn^{2+}$ AMPPMP and E.$Mn^{2+}$DPM complexes were taken under conditions where the ligand/$Mn^{2+}$ ratio was optimized to remove non-specific relaxation effects. The spectra revealed small, well-defined sets of residues (20 and 33 for the .AMPPNP and .DPM complexes, respectively) that "vanished" upon insertion of $Mn^{2+}$, and that the sets were non-overlapping, with the exception of three resonances. The resonances that disappear in the presence of $Mn^{2+}$ were traced back to cross-peaks in the apo spectrum and numbered, the three common cross-peaks are boxed, see FIG. 3. These assignments must remain tentative until the spectra are assigned fully. This figure demonstrates the high resolution that can be achieved at 900 Mz using $^{15}$N, $^{13}$C, $^2$H-labelled MK—each of the predicted 282 backbone amide resonances is resolved.

Again, NMR results corroborate the non-crystallographic finding of essentially independent ligand-binding sites. The three overlapping cross-peaks offer the intriguing reminder that the allosteric and active-sites communicate, and that the phosphoryl-transfer chemistry is disrupted by the binding of DPM. These peaks might well correspond to important shared elements of the molecular switch that derails the chemistry. Comparing the ternary and ternary.DPM structures can pin-point precisely how that disruption occurs. Once amide backbone resonances are assigned to the primary sequence of MK, the $Mn^{2+}$-sensitive residues can be mapped onto the crystal structure to begin to define the DPM-binding site.

Diphosphomevalonate decarboxylase (DPM-DC).

This complex enzyme catalyzes three, coupled chemical reactions to decarboxylate mevalonate diphosphate and cleave the β,γ-bond of ATP. The reaction sequence begins with nucleophilic attack of the DPM $C_3$-hydroxyl at the γ-phosphate of ATP, forming a phosphorylated intermediate and ADP. The $C_3$—OP bond of the intermediate is then heterolytically cleaved such that the electron pair departs with phosphate. The loss of negative charge attending electron departure produces a carbocation that draws electrons ultimately from the carboxylate oxygen(s), resulting in cleavage of the $C_1$-$C_2$ bond, to form $CO_2$ and the double bond of isopentenyl diphosphate (IDP). DPM-DC appears to be the only example of decarboxylase capable of recruiting a nucleotide (ATP), or, more precisely, its γ-phosphoryl group, to act as an electron-sink cofactor in a β-elimination decarboxylation reaction. The carbocation-based mechanism underlying this chemistry is also distinct among enzymatic decarboxylation reactions. It is interesting to note that Nature seems to have crafted a mechanistically unique catalyst for this single point in metabolism—the gateway for isoprenoid biosynthesis. Thus, apart from its considerable metabolic significance, the uniqueness the DPM-DC mechanism recommends it well for further scrutiny.

The art provides several fundamental aspects of the chemical mechanism of the enzyme. For instance, DPM $^{18}$O-labelled at the $C_3$-hydroxyl was used to demonstrate that the phosphate produced by the reaction is formed by heterolytic cleavage of the $C_3$—O bond, rather than hydrolysis (i.e., $PO_4$ contained the $^{18}$O originally present at the $C_3$-hydroxyl). (Lindberg M, Yuan C, Dewaard A, Bloch K. 1962. On the mechanism of formation of isopentenylpyrophosphate. *Biochemistry* 1: 182-8.) Elegant isotopic labeling experiments convincingly demonstrate that $CO_2$ and $PO_4$ eliminate from the phosphorylated intermediate in trans; that is, the two σ-bonds broken in the elimination reactions are, or are nearly, antiparallel to one another when the elimination occurs. (Cornforth J W, Cornforth R H, Popjak G, Yengoyan L. 1966. Studies on the biosynthesis of cholesterol. Steric course of decarboxylation of 5-pyrophosphomevalonate and of the carbon to carbon bond formation in the biosynthesis of farnesyl pyrophosphate. *J. Biol. Chem.*, 241: 3970-87.) Using $(S_p)$-[γ-$^{17}O_2$, $^{18}$O]ATPγS Frey et. al. demonstrated that the stereochemistry of the γ-phosphate of ATP is retained in the thiophosphate produced by the reaction, suggesting that the mechanism involves, nominally, a single in-line displacement at phosphorous, caused by attack of the $C_3$-hydroxyl. (Iyengar R, Cardemil E, Frey P A. 1986. Mevalonate-5-diphosphate decarboxylase: stereochemical course of ATP-dependent phosphorylation of mevalonate 5-diphosphate. *Biochemistry*, 25: 4693-8.)

Figure 4:
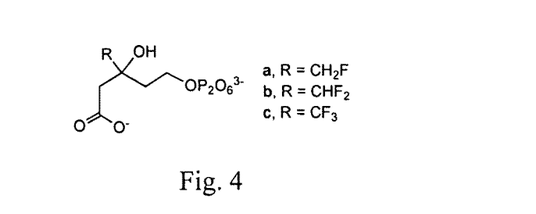
FIG. 4. $C_6$-fluoro substituted DPM analogues. Potent inhibitors of DPM-DC.

A set of compounds designed to inhibit, and probe the mechanism of DPM-DC: a graduated series of fluorine-substituted compounds in which one, two or three of the $C_6$-methyl protons of DPM are replaced with fluorine, FIG. 4. (Reardon J E, Abeles R H. 1987. Inhibition of cholesterol biosynthesis by fluorinated mevalonate analogues. *Biochemistry*, 26: 4717-22; Dhe-Paganon S, Magrath J, Abeles R H. 1994. Mechanism of mevalonate pyrophosphate decarboxy- lase: evidence for a carbocationic transition state. *Biochemistry*, 33: 13355-62.) The mono-fluoro derivative turns over at 0.19 $min^{-1}$—0.04% that of the native compound. Fluorine substitution is expected to accelerate decarboxylation via a carbanion mechanism because increasing electron withdrawal stabilizes the negative charge transfer that occurs during carbanion formation. While the dramatic (2500-fold) decrease in turnover caused by mono-fluoro substitution at $C_6$ strongly disfavors a carbanion mechanism, it strongly supports a carbocation mechanism, in which the electron withdrawing effects of fluorine destabilize the development of positive charge at $C_3$ associated with the departure of phosphate.

Figure 5:
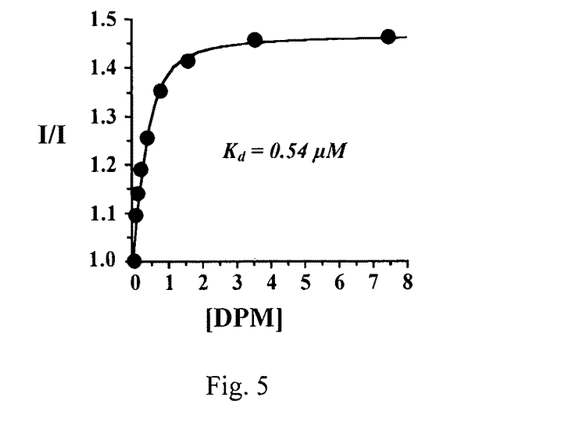
FIG. 5. DPM Binding to DPM-DC. Conditions: DPM-DC (0.10 µM); $MgCl_2$ (1.0 mM); β-Me (2.0 mM); KCl (50 mM); Glycerol (0.5% v/v); Hepes (50 mM, pH 8.0); T=25 (±2)° C.

The binding of DPM causes a 1.5-fold change in the intrinsic fluorescence of DPM-DC (FIG. 5); $K_d$ for this interaction is 0.54 (±0.03) µM. This spectroscopic handle can be used to determine the affinities of the inhibitors described in this proposal and to explore the mechanism of DPM-DC. Fluorescence-based screening is efficient and can succeed (by competition vs DPM) even when the inhibitor does not cause a fluorescence change. In certain situations, it may prove advantageous to identify the enzyme form (E or E.AMPPNP) to which an inhibitor binds most tightly. As a tool to study mechanism, the DPM-induced fluorescence changes can monitor, by stopped-flow, the progress of the binding reactions. The concentration dependencies of such measurements yield microscopic rate constants, which, in turn, provide ground and transition-state energetics for a particular step in the reaction coordinate. In favorable cases, fluorescence changes occur subsequent to binding as consequence of other structural changes that occur during the catalytic cycle—such is the case with DPM-DC. These changes can be assigned to bond-cleavage steps using by monitoring chemistry in the presteady-state by quenched-flow.

Design and Synthesis of Inhibitors.

Irreversible, covalent enzyme inhibition is capable of efficient inactivation of microorganism pathways over long periods of time. Generally, high selectivity of the inhibitor by the pathogen vs the host isozyme is important; however, inhibition of the cholesterol pathway in man is not deleterious, as is evidenced by the widespread use of statin drugs for lowering cholesterol levels. These drugs inhibit cholesterol biosynthesis at the step just prior to MK. Furthermore, antibacterial drugs are typically administered for short periods of time, avoiding the long-term side effects associated with chronic therapy.

Mindful of such consideration, scheme 1 presents a carbocation-based mechanism for the DPM-DC reaction. ATP phosphorylates DPM to 3-phosphoDMP (1), which ionizes to carbocation 2 followed by decarboxylation to isopentenyl diphosphate (3). Intermediate 2 is written as a free carbocation, but decarboxylation is most likely concomitant with the development of carbocation character. Strong support for this mechanism comes from the finding that remote electron-withdrawing groups increase the rate of concerted decarboxylation and elimination (E2) reactions. (Knipe A C, Stirling C J M. 1968. Elimination-Addition. Part XV. Rates of reactions of ω-bromoalkyl p-tolyl sulphides with alkoxides: The role of neighbouring group participation by sulphur and the involvement of ion-pair equilibria. *J. Chem. Soc.*, (B) 1218-23; Knipe A C, Stirling C J M. 1967. Elimination-Addition. Part XIII. Reactions of -bromoalkyl p-tolyl sulphones with bases: The role of inductive effects in elimination and substitution. J. Chem. Soc., (B): 808-13, 1967.) If an E2 mechanism were operative in the DPM-DC system, (i.e., no intermediate 2 in Scheme 1), the fluoromethyl-DPM analogues would be better, not far slower, substrates than DPM. Based on this mechanism, two potential inactivators are proposed (4 and 5), and their expected inactivation mechanisms are given in Schemes 2 and 3.

Following phosphorylation to form the intermediates 6 and 10, ionization produces a highly reactive carbocation intermediate (7 or 11) that undergoes nucleophilic attack by an active site residue ($X^-$), leading to irreversible inactivation of the enzyme (8 or 12). Intermediates 7 and 11 are more reactive than purported intermediate 2 with the normal substrate because they have primary carbocation character. Typically, enzymes that catalyze reactions that proceed by carbocation intermediates have aromatic- or carbonyl-containing residues near the incipient carbocation to stabilize the intermediate.

The vinyl and cyclopropyl groups should not sterically interfere with binding if the bacterial enzyme active site is similar to that of the mammalian enzyme; DPM with an ethyl instead of a methyl group (14) is a good substrate for mammalian DPM decarboxylase with a $K_m$ of 33 µM (DPM is 15 µM) and a $k_{cat}$ 32% that of DPM ($k_{cat}/k_m$ about ⅙ that of DPM). (Reardon J E, Abeles R H. 1987. Inhibition of cholesterol biosynthesis by fluorinated mevalonate analogues. *Biochemistry,* 26: 4717-22.)

The syntheses of 4 and 5 proceed through a common intermediate (19), as shown in Scheme 4. Diethyl acetonedicarboxylate is protected as the ethylene glycol ketal (15). (Bell A, Davidson A H, Earnshaw C, Norrish H K, Torr R S, Trowbridge D B, Warren S. 1983. Synthesis of β-(diphenylphosphinoyl) ketones. *J. Chem. Soc. Perkin Trans.,* 1: 2879-91.) Lithium aluminum hydride reduction of 15 gives 16, protected first with a tert-butyldimethylsilyl group (17) then with a p-methoxybenzyl group (18), which can be deprotected under conditions that do not affect the silyl protecting group. (Yamashita A, Toy A, Scahill T A. 1989. Synthesis of khellin and its analogs via chromium carbene complexes. *J. Org. Chem.,* 54: 3625-34; Kazuta Y, Matsuda A, Shuto S. 2002. Development of Versatile cis- and trans-Dicarbon-Substituted Chiral Cyclopropane Units: Synthesis of (1S,2R)- and (1R,2R)-2-Aminomethyl-1-(1H-imidazol-4-yl)cyclopropanes and Their Enantiomers as Conformationally Restricted Analogues of Histamine. *J. Org. Chem.,* 67: 1669-77; Chênevert R, Dasser M. 2000. Chemoenzymatic Synthesis of the Microbial Elicitor (−)-Syringolide via a Fructose 1,6-Diphosphate Aldolase-Catalyzed Condensation Reaction. 65: 4529-31.) Mild acid hydrolysis of the ketal leaves the two alcohol protecting groups intact, giving the common intermediate 19. (Lesburg C A, Zhai G, Cane D E, Christianson D W. 1997. Crystal structure of pentalenene synthase: mechanistic insights on terpenoid cyclization reactions in biology. *Science,* 277: 1820-4.) Treatment of 19 with either vinylmagnesium bromide or cyclopropylmagnesium bromide gives 20 or 24, respectively. (Overman L, Nan-Horng L. 1985. Enantioselective total synthesis of (+)-pumiliotoxin A. *J. Org. Chem.,* 50: 3669-70; Wong K-T, Hung Y-Y. 2003. A convenient one-pot synthesis of homoallylic halides and 1,3-butadienes. *Tetrahedron Lett.,* 44: 8033-6) 50: 3669-70.) Removal of the p-methoxybenzyl group by DDQ oxidation gives the primary alcohol (21), which is oxidized to the corresponding acid (22) with pyridinium dichromate. (Chênevert R, Dasser M. 2000. Chemoenzymatic Synthesis of the Microbial Elicitor (−)-Syringolide via a Fructose 1,6-Diphosphate Aldolase-Catalyzed Condensation Reaction. 65: 4529-31; Corey E J, Schmidt G. 1979 Useful procedures for the oxidation of alcohols involving pyridinium dichromate in aprotic media. *Tetrahedron Lett.,* 20: 399-402.) Silyl group deprotection with tetra-n-butylammonium fluoride gives the mevalonic acid analogue 23 or 25, which can be converted to the corresponding diphosphates (4 or 5, respectively) by the known procedure. (Kazuta Y, Matsuda A, Shuto S. 2002. Development of Versatile cis- and trans-Dicarbon-Substituted Chiral Cyclopropane Units: Synthesis of (1S,2R)- and (1R,2R)-2-Aminomethyl-1-(1H-imidazol-4-yl)cyclopropanes and Their Enantiomers as Conformationally Restricted Analogues of Histamine. *J. Org. Chem.,* 67: 1669-77; Reardon J E, Abeles R H. 1987. Inhibition of cholesterol biosynthesis by fluorinated mevalonate analogues. *Biochemistry,* 26: 4717-22)

Scheme 4

-continued

6-Fluoromevalonic acid is a substrate for MK and PMK, producing 6-fluoroDPM (see above). Therefore, 23 and/or 25 also may be substrates for these enzymes and produce 4 and/or 5, respectively, without the need for chemical conversion. Compounds 23a and 25a, which are much more bioavailable than 4 and 5, can then be used as prodrugs in much the same way that $F_3$-mev was used as a precursor of $F_3$-DPM to kill S. pneumoniae (see above).

The diphosphates, 4 and 5, can be tested as mechanism-based inhibitors of DPM-DC. Time-, concentration-, and ATP-dependent inhibition can be investigated, then irreversibility can be determined by fluorescence titration. As 4 and 5 prove to be irreversible inhibitors, giving 8 and 12, respectively, their sites of attachment can be determined using several approaches. Electrospray ionization mass spectrometry can be used to quantify the change in mass that occurs following inactivation to show that a molecule became attached to the enzyme. Proteolytic digestion followed by mass spectrometry can be used to identify the modified fragment(s), and these modified peptide fragments can be sequenced by mass spectrometry. Alternatively, HPLC difference maps can be used to identify the modified peptide fragments, which can be purified and submitted for Edman degradation analysis to identify the attachment site. Because of the difference in geometry between a vinyl group and a cyclopropyl group, the X group in 8 and 12 need not be the same. It may be possible to use different proteases to identify a likely attachment site, which will be tested by mutagenesis (assuming the mutant is active). Concurrent with the mass spectral approach, the inactivated enzyme can be crystallized to definitively assign the attachment site and confirm the adduct structure.

As discussed, DPM is a selective, noncompetitive inhibitor of the S. pneumoniae MK. Accordingly, because of the structural similarities of 4 and 5 to DPM, these compounds can be used as inhibitors of S. pneumoniae and human MK to determine if either compound binds to the allosteric site of the bacterial enzyme. With observation of non-competitive inhibition, the structure of the inhibitor bound to the active site can be obtained by NMR spectrometry or X-ray diffraction, and used for design of analogues. Either of these synthetic molecules would be a better choice for further development as a medicinal agent than DPM. If the non-phosphorylated precursors of 4 and 5 are substrates for MK, they will also be inhibitors. The ultimate goal for these compounds is that they serve a dual inhibitory function: competitive inhibitors and substrates of MK, which converts them (in conjunction with PMK) to 4 and 5, which inhibits both MK (allosterically) and DPM-DC. In this scenario, the compounds shut down the pathway at two points in multiple ways. The initial biological results of such compounds can be the basis for further molecular design.

Figure 6:
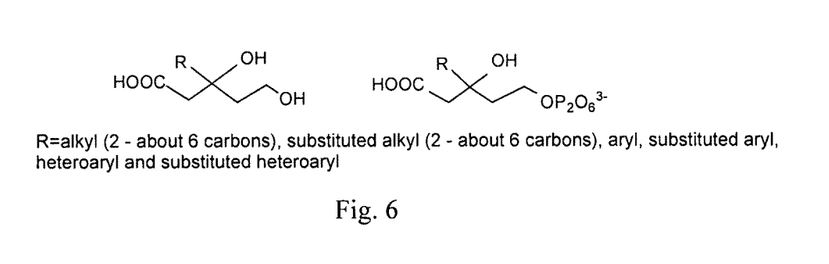
FIG. 6. Two non-limiting series of compounds for inhibition of MK and DPM-DC.
Figure 7:
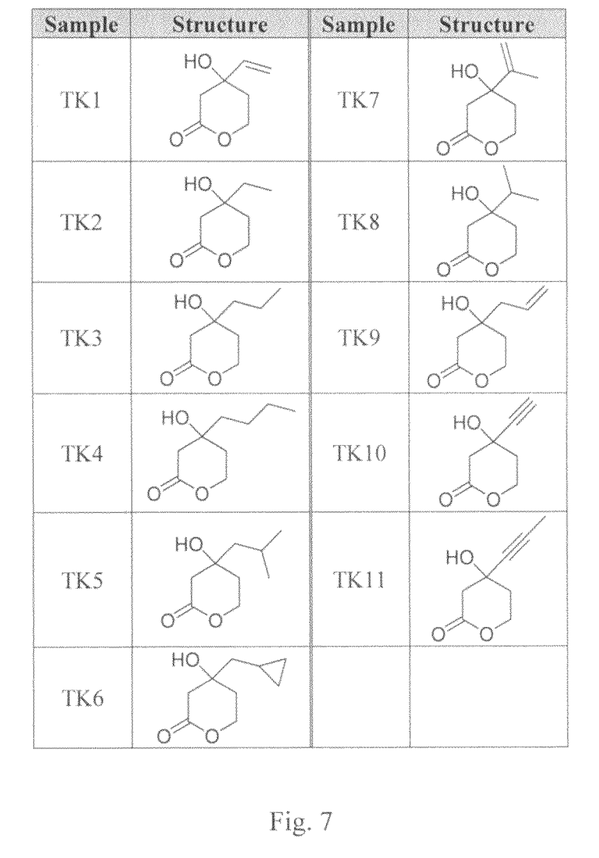
FIG. 7. Representative, non-limiting inhibitor compounds.
Figure 8:
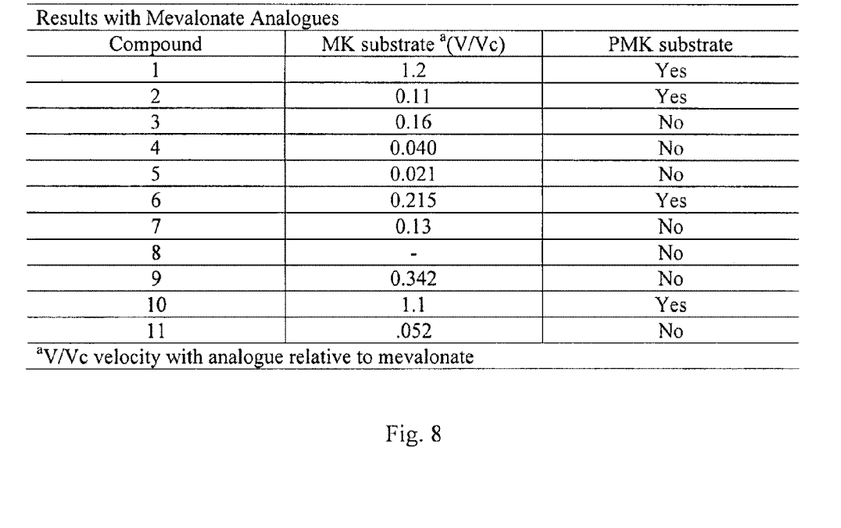
FIG. 8. Initial substrate results [analogue] ranged from 2.0-2.5 mM, except #6 (4.2 mM) and #8 (6.2 mM). [ATP]= Km=0.85 mM. $k_{cat}$ with mevalonate=227 s$^1$.

A series of compounds related to compounds 4, 5, 23, and 25 can be synthesized as potential competitive or noncompetitive reversible inhibitors of MK and DPM-DC (See, e.g., FIGS. 6-7). The representative synthesis shown (Scheme 4a) is a modification of that shown in Scheme 4, and R is limited only by availability of the corresponding reagent and synthetic technique, as would be understood by those skilled in the art made aware of this invention (e.g., alkyl, vinyl, acetylenyl, aryl, heteroaryl, etc., via Grignard reaction with the corresponding magnesium bromide or chloride). Results indicative of the utility of this invention and demonstrating effective treatment of Streptococcus pneumoniae, as would be understood by those skilled in the art, are provided in FIG. 8, with reference to FIG. 7. Preliminary data shows compounds 10 and 11 are especially effective as substrates for mevalonate kinase, with compound 4 as a substrate for phosphomevalonate kinase.

Scheme 4a

We claim:

1. A mevalonate pathway inhibitor compound of a formula wherein $R_1$ is selected from $C_2$ to $C_6$ alkenyl, $C_2$ to $C_6$ alkynyl, aryl, and heteroaryl moieties; and $R_2$ and $R_{2'}$ are independently selected from H, monophosphate and diphosphate moieties; and salts, esters, hydrates and solvates thereof.

2. The inhibitor compound of claim 1 wherein $R_1$ is selected from vinyl and acetylenyl moieties.

3. The inhibitor compound of claim 1 wherein $R_2$ and $R_{2'}$ are H.

4. A compound of a formula wherein $R_1$ is selected from aryl, and heteroaryl moieties; and $R_2$ and $R_{2'}$ are independently selected from H, monophosphate and diphosphate moieties; and salts, esters, hydrates and solvates thereof.

5. The compound of claim 4 wherein $R_1$ is selected from $C_2$ to $C_3$ alkenyl moieties.

6. The compound of claim 4 wherein $R_1$ is selected from cyclopropyl and methylenecyclopropyl moieties.

7. The compound of claim 4 wherein $R_1$ is selected from vinyl and acetylenyl moieties.

* * * * *